United States Patent
Eom et al.

(10) Patent No.: US 7,310,140 B2
(45) Date of Patent: Dec. 18, 2007

(54) METHOD AND APPARATUS FOR INSPECTING A WAFER SURFACE

(75) Inventors: Tae-Min Eom, Sungnam-si (KR); Yu-Sin Yang, Sungnam-si (KR); Chung-Sam Jun, Suwon-si (KR); Yun-Jung Jee, Yongin-si (KR); Joung-Soo Kim, Gyeonggi-do (KR); Moon-Kyung Kim, Goyang-si (KR); Sang-Mun Chon, Yongin-si (KR); Sun-Yong Choi, Sungnam-si (KR)

(73) Assignee: Samsung Electronics Co., Ltd. (KR)

( * ) Notice: Subject to any disclaimer, the term of this patent is extended or adjusted under 35 U.S.C. 154(b) by 194 days.

(21) Appl. No.: 10/877,684

(22) Filed: Jun. 25, 2004

(65) Prior Publication Data

US 2004/0263836 A1 Dec. 30, 2004

(30) Foreign Application Priority Data

Jun. 30, 2003 (KR) .................... 10-2003-0043232

(51) Int. Cl.
*G01N 21/00* (2006.01)
(52) U.S. Cl. .............................. 356/237.4; 356/237.5; 356/237.2
(58) Field of Classification Search .. 356/237.1–237.6, 356/394, 71–73; 250/559.4, 559.45, 221, 250/221.1, 222, 458.1, 459.1, 201.6
See application file for complete search history.

(56) References Cited

U.S. PATENT DOCUMENTS

| | | | |
|---|---|---|---|
| 4,598,997 A * | 7/1986 | Steigmeier et al. ...... 356/237.5 |
| 4,748,335 A * | 5/1988 | Lindow et al. ......... 250/559.22 |
| 5,189,481 A * | 2/1993 | Jann et al. ..................... 356/73 |
| 5,293,538 A * | 3/1994 | Iwata et al. .............. 356/239.1 |
| 6,122,046 A * | 9/2000 | Almogy ................... 356/237.2 |
| 6,399,957 B1 * | 6/2002 | Murata ..................... 250/559.4 |
| 6,534,774 B2 * | 3/2003 | Hasegawa et al. ....... 250/458.1 |
| 6,597,006 B1 * | 7/2003 | McCord et al. ........ 250/559.19 |
| 6,791,009 B1 * | 9/2004 | Pandey et al. .............. 800/282 |
| 6,798,504 B2 * | 9/2004 | Sato et al. ............... 356/237.2 |

FOREIGN PATENT DOCUMENTS

| JP | 11176735 | 12/2000 |
|---|---|---|
| JP | 10-0253054 | 7/2001 |
| KR | 1999-0081401 | 11/1999 |

* cited by examiner

*Primary Examiner*—Sang H. Nguyen
(74) *Attorney, Agent, or Firm*—F. Chau & Assoc., LLC (57) ABSTRACT

In a method and an apparatus for inspecting a wafer surface, a wafer is loaded into a chamber. An incident light including a first light for sensing a vertical position of the wafer and a second light for inspecting the wafer surface is irradiated onto the wafer. The first light is reflected on an inspection region or a next inspection region of the wafer and is detected to control a wafer position. The second light is scattered on the inspection region and is detected to inspect the wafer surface of the inspection region. Position information of a wafer is examined and a position of the wafer is adjusted before inspecting a surface of inspection region of a wafer so as to enable accurate inspection of the wafer surface.

21 Claims, 11 Drawing Sheets

METHOD AND APPARATUS FOR INSPECTING A WAFER SURFACE

CROSS-REFERENCE TO RELATED APPLICATION

This application claims priority to Korean Patent Application No. 2003-43232 filed on Jun. 30, 2003, the contents of which are herein incorporated by reference in its entirety.

BACKGROUND OF THE INVENTION

1. Technical Field

The present disclosure relates to a method and an apparatus for inspecting a wafer surface. More particularly, the present disclosure relates to a method for automatically adjusting a position in a dark field inspection apparatus to inspect a wafer surface and an apparatus for performing same.

2. Discussion of the Related Art

As design scales become minute, trivial defects that were not critical previously become critical, thereby resulting in lower productivity. Therefore, an inspection apparatus having extended precision is required. Additionally, a method of precisely controlling the apparatus is required.

In a process of manufacturing a semiconductor device, an inspection process may be classified into three sub processes.

A first sub process is an efficiency inspection of an inspection apparatus. A criterion wafer is loaded in the inspection apparatus. Then, an inspected value is obtained and compared with a criterion value of the criterion wafer to examine the efficiency of the inspection apparatus.

A second sub process is an inspection to detect a cause of abruptly lowered productivity.

A third sub process is an inspection to detect defects of a wafer that has undergone some of the manufacturing process.

One of the known apparatuses for inspecting a wafer surface uses laser scattering. A laser is irradiated at a predetermined angle onto a surface of an objective wafer that is to be inspected. Then, a scattered laser caused by defects on the wafer surface is detected to examine defects. The laser is irradiated onto the objective wafer by the Raster scan method, and the laser has a specific spot size. Therefore, in order to scan the entire surface of the objective wafer, a plurality of the Raster scannings may be performed thereon.

In detecting the scattered laser, a detector having mirrors that condense the scattered laser and a photo multiplier tube (PMT) may be used. The PMT outputs an electric serial signal having a varying amplitude in accordance with the strength of the scattered laser. Then, a computer analyzes the outputted electric serial signal. When an electric serial signal that exceeds a limit is detected, the objective wafer is judged to have defects.

In examining whether or not the laser is irradiated on the wafer exactly, an auto position system (APS) may be used. The APS not only detects a position where the laser is reflected according to height difference of the wafer, but also detects the height difference.

Figure 1:
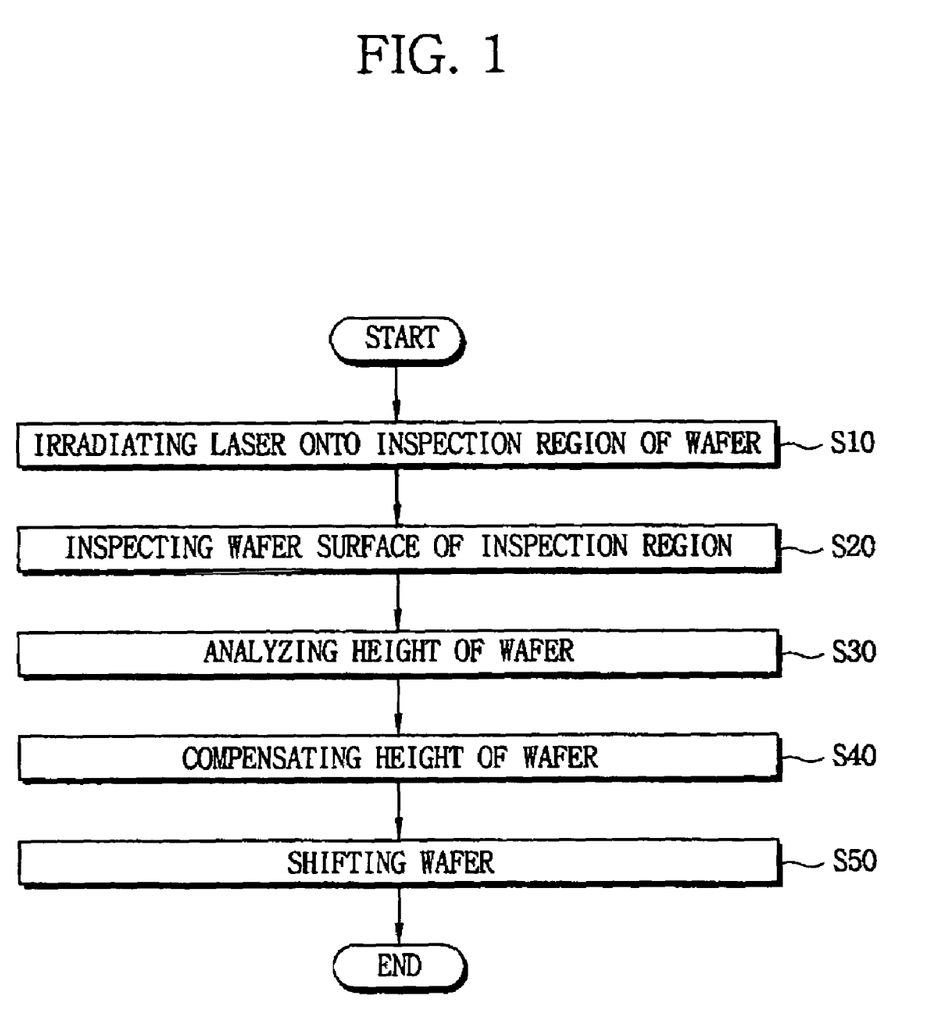
FIG. 1 is a flow chart showing a conventional method of inspecting a wafer surface.

FIG. 1 is a flow chart showing a conventional method of inspecting a wafer surface.

Referring to FIG. 1, in step S10, a wafer is loaded in an apparatus for inspecting a wafer surface, and a laser is irradiated onto an inspection region of a wafer. Then, in step S20, a portion of the laser may be scattered on an inspection region of the wafer, and a detector detects the scattered laser to inspect a surface of the inspection region of the wafer. In step S30, a remaining portion of a laser that is reflected on the wafer surface of the inspection region is detected in order to analyze a height of the wafer. Then, in step S40, the height of the wafer is compensated for by position analysis. Then, in step S50, the wafer is shifted parallelly in order to inspect a wafer surface of a next inspection region of the wafer.

According to the conventional method of inspecting a wafer surface, a height of the inspection region, which is detected during inspection of the inspection region, is fed back to compensate for a height of the next inspection region. Likewise, a height of the next inspection region is used for compensating for a height of a third chip, and so on. Therefore, when a height of the first inspection region is deviated far from an allowable limit, after a large number of chips are inspected, many chips of the wafer will be unreliable, thereby lowering productivity.

SUMMARY OF THE INVENTION

An embodiment of the present invention provides a method for inspecting a wafer surface, capable of promptly compensating for a height of a chip during inspection of the chip.

Another embodiment of the present invention provides an apparatus for inspecting a wafer surface, capable of promptly compensating for a height of a chip during inspection of the chip.

According to an embodiment of the present invention, a method for inspecting a wafer surface, comprises loading a wafer into a chamber, irradiating a light incident on the wafer, the light including a first light for sensing a vertical position of the wafer and a second light for inspecting the wafer surface is irradiated onto the wafer, detecting the first light reflected on an inspection region or a next inspection region of the wafer to control a wafer position, and detecting the second light scattered on the inspection region to inspect the wafer surface of the inspection region.

The first and second lights may be alternately irradiated. The wafer position may be controlled by transforming the detected first light into a position information signal, obtaining a position compensating value by comparing the position information signal and a reference information signal, generating an electric signal for adjusting a position of the wafer on a basis of the position compensating value, and adjusting the position of the wafer by using the electric signal.

The surface of the inspection region may be inspected by generating an image information signal from the scattered second light, checking defects of the surface of the inspection region based on the image information signal, and shifting the wafer in a predetermined direction to align the wafer for control of the position of the wafer. The predetermined direction may be the horizontal direction.

Generating the image information signal may comprise transforming the scattered second light into a first signal containing information of the surface of the inspection region, generating a second signal by compensating for an interval caused by alternately irradiated incident light, compensating for a phase of the second signal with a clock, generating a third signal having a phase synchronized with a phase of the second signal, generating a square wave corresponding to a time interval of the second light included in the third signal, outputting a signal corresponding to the time interval of the second light by controlling the square wave, and digitalizing the signal corresponding to the time interval of the second light to output the image information signal.

The first and second lights may have different wavelengths from each other, and the first and second lights may be simultaneously irradiated. Control of the wafer position and inspection of the surface of the inspection region may be simultaneously performed by detecting the first light reflected on the inspection region while simultaneously detecting the second light scattered on the inspection region, generating a position information signal in accordance with the first light reflected on the inspection region and an image information signal in accordance with the second light scattered on the inspection region, adjusting a vertical position of the wafer, and shifting the wafer in a horizontal direction to align the wafer for further control of the wafer position. The first and second lights may have the same frequency and a circular cross-sectional shape having a specific area.

The wafer position may be controlled by analyzing a vertical position and an incline of the wafer with the first light reflected on the inspection region for anticipating a vertical position and an incline of the next inspection region, generating an image information signal from the second light scattered on the inspection region, shifting the wafer, whereby the next inspection region is moved to a position formerly occupied by the inspection region, and adjusting the vertical position and the incline of the wafer by the anticipated vertical position and incline. Anticipating the vertical position and the incline of the next inspection region may comprise generating a first electric signal containing the vertical position and the incline of the wafer, converting the first electric signal into a square wave, generating a pulse series corresponding to a width of the square wave, counting the number of the pulse series to output a pulse number corresponding to a pulse disposed at a center of the square wave and to a width of the pulse, forming an image having a circular shape in accordance with the width and the center of the square wave, and comparing the image and a reference image to obtain compensation values for the next inspection region of the wafer.

According to another embodiment of the present invention, an apparatus for inspecting a wafer surface, comprises a wafer moving section, an optical system, a position sensing section, an image sensing section and a feedback circuit. The wafer moving section moves a wafer in vertical and horizontal directions. The optical system irradiates an incident light including a first light for sensing a vertical position of the wafer and a second light for inspecting the wafer surface. The position sensing section senses the first light reflected on the wafer to generate a position information signal that is digitalized. The image sensing section senses the second light scattered on the wafer to generate an image information signal. The feedback circuit generates a value for adjusting a vertical position of the wafer. The feedback circuit provides the wafer moving section with the value to adjust the position of the wafer.

Irradiation of the first and second lights may be repeated discontinuously. The optical system may comprise a chopper for generating the first and second lights, the chopper comprising a rotational axis, a first opening for transmitting incident light, the incident light passing through the first opening for forming the first light, and a second opening for transmitting the incident light, the incident light passing through the second opening for forming the second light.

The image sensing section may comprise a light sensor for sensing the second light scattered on the wafer to generate a first signal containing information about the wafer surface, a level compensator for compensating a time interval caused by discontinuity of the light incident on the wafer to generate a compensated value, a mixer for mixing the first signal generated from the light sensor and the compensated value generated from the level compensator to form a second signal that is continuous, a clock generator for generating a clock signal, a phase locked loop for receiving the second signal from the mixer and the clock signal from the clock generator, the phase locked loop synchronizing the clock signal with the second signal to generate a third signal, a counter for receiving the clock signal synchronized with the second signal to generate a square wave, a signal control section for receiving the third signal to generate a fourth signal corresponding to a time interval of the second light under a control of the square wave generated from the counter, and an analog-digital converter for digitalizing the fourth signal to output the image information signal.

The optical system may generate at least two lights incident on the wafer, the at least two lights having different wavelengths from each other. The at least two lights may comprise the first light irradiated onto a next inspection region of the wafer to sense the vertical position of the wafer, and the second light irradiated onto an inspection region of the wafer to inspect the wafer surface of the inspection region.

The light irradiated from the optical system may have a specific cross-sectional area. The position sensing section may comprise a light sensor for sensing light for generating a first electric signal containing information including the vertical position and an incline of the wafer, a regulator for receiving the first electric signal for generating a square wave, a timer for outputting a pulse series corresponding to a width of the square wave, a pulse counter for counting a number of the pulse series, and a clock generator for providing the timer and the pulse counter with a clock signal.

The feedback circuit may comprise an image processor for generating compensated values of the vertical position and an incline of the wafer in accordance with an image of an inspection region. The light incident on the wafer may correspond to a laser having a wavelength ranging from about 360 nm to about 1 μm. A mirror may reflect the first light reflected on the wafer toward the position sensing section. The wafer moving section may comprise a motor for roughly adjusting the wafer by the value for adjusting the vertical position of the wafer, and a piezoelectric device for precisely adjusting the wafer.

The feedback circuit may comprise a processor for generating the value for adjusting the vertical position of the wafer and for checking for defects of an inspection region of the wafer by image processing, a system controller for receiving the value for adjusting the vertical position of the wafer and for providing the wafer moving section with an analog signal, and a bus line for electrically connecting the processor and the system controller for transferring an electric signal between the processor and the system controller. The apparatus may also comprise a memory section for storing the value for adjusting the vertical position of the wafer, wherein the feedback circuit is electrically connected to the bus line.

In accordance with at least one embodiment of the present invention, position information of a wafer is examined and a position of the wafer is adjusted before inspecting a surface of inspection region of a wafer. Therefore, inspection of wafer surface is precisely performed.

BRIEF DESCRIPTION OF THE DRAWINGS

Preferred embodiments of the present invention can be understood in more detail from the following descriptions taken in conjunction with the accompanying drawings, in which.

DETAILED DESCRIPTION OF THE PREFERRED EMBODIMENTS

Preferred embodiments of the present invention will be described below in more detail with reference to the accompanying drawings. This invention may, however, be embodied in different forms and should not be construed as limited to the embodiments set forth herein. Rather, these embodiments are provided so that this disclosure will be thorough and complete, and will fully convey the scope of the invention to those skilled in the art.

Figure 2:
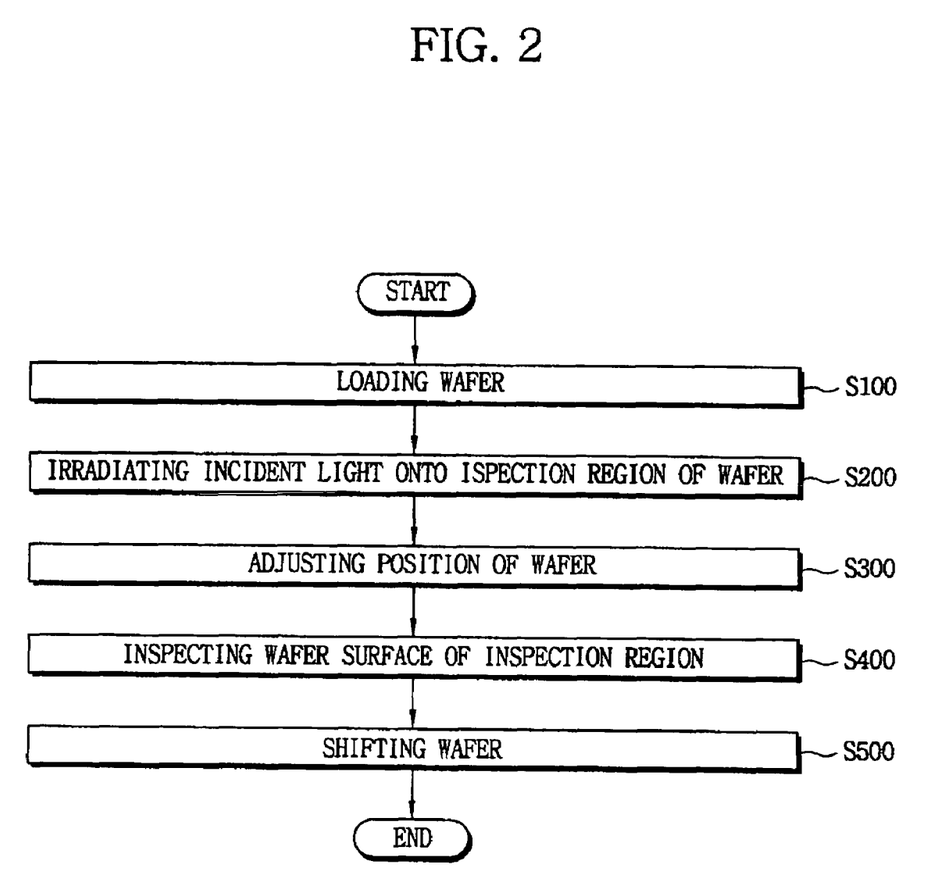
FIG. 2 is a flow chart showing a method of inspecting a wafer surface according to a first embodiment of the present invention.
Figure 3:
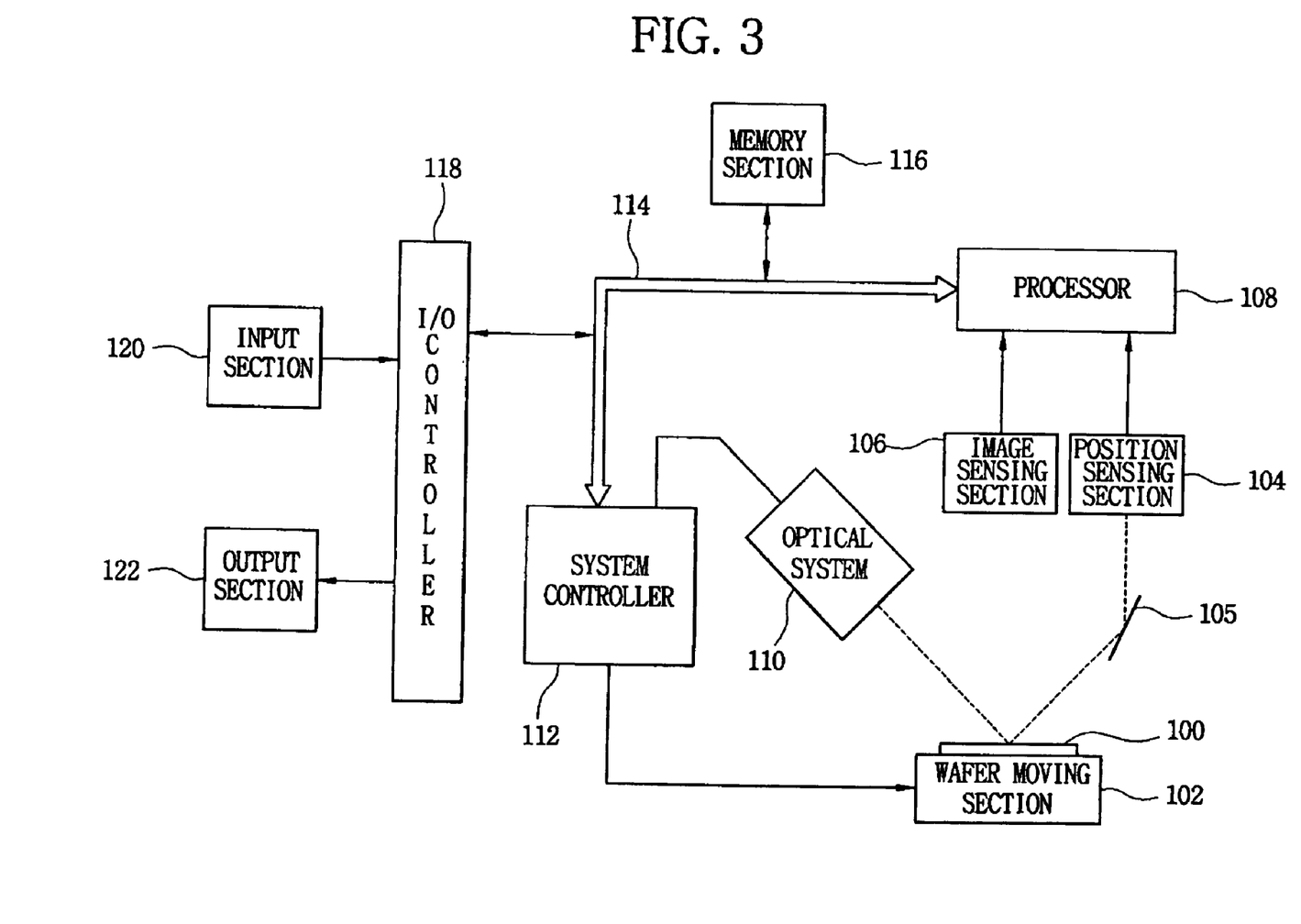
FIG. 3 is a schematic view showing an apparatus for inspecting a wafer surface according to a first embodiment of the present invention.

FIG. 2 is a flow chart showing a method of inspecting a wafer surface according to an embodiment of the present invention, and FIG. 3 is a schematic view showing an apparatus of inspecting a wafer surface according to a first embodiment of the present invention.

Referring to FIG. 2, in step S100, a wafer that is to be inspected is loaded into the inspection apparatus. In step S200, a laser is then irradiated onto an inspection region of the objective wafer. A portion of the laser is scattered and a remaining portion of the laser is reflected on the inspection region. In step S300, the laser reflected on the inspection region is detected to analyze height of the inspection region, and in step S300, a height of the inspection region is adjusted. Then in step S400, an inspection of a surface of the inspection region is performed.

In detail, the inspection of a surface of the inspection region is performed as follows. The scattered laser is detected to form an image. Then, the image is converted into digital code by an encoding process, and the encoded digital code is compressed via data compression. A portion of the compressed digital code, which corresponds to high frequency and noise, is eliminated. The compressed digital code may correspond to a Joint Photographic Experts Group (JPEG) or a Motion Picture Experts Group (MPEG).

When the inspection of the inspection region of the wafer is completed, the wafer is shifted in a substantially parallel direction such that a next inspection region adjacent to the inspection region is inspected in step S500, and the same procedures are repeated for the next inspection region.

The laser that is irradiated onto the wafer may include two rays. The two rays may be arranged in series or in parallel. The ray that is irradiated onto the wafer may have a specific spot size to analyze the position of the next inspection region.

Referring to FIG. 3, an apparatus for inspecting a wafer surface according to the first embodiment of the present invention includes a wafer moving section 102, a position sensing section 104, an image sensing section 106, a processor 108, an optical system 110, a system controller 112, a memory section 116, an input/output (I/O) controller 118, an input section 120 and an output section 122.

The optical system 110 forms a laser and the optical system 110 irradiates the laser onto a wafer 100. The optical system may include a chopper that divides the laser into two rays arranged in series. The laser has a wavelength that ranges from about 360 nm to about 1 µm. The optical system may include two laser generators arranged substantially parallel to each other to irradiate two substantially parallel laser rays.

The wafer moving section 102 supports the wafer 100, and the wafer moving section 102 moves the wafer 100 parallel (or in a horizontal direction) or vertically (or in a vertical direction). The wafer moving section 102 includes a motor for moving the wafer, and a piezoelectric device for accurate vertical position control of the wafer.

The position sensing section 104 senses a first portion of the laser, which is reflected on the wafer, and the position sensing section 104 generates a digitalized position signal according to the first portion of the laser. The digitalized position signal is provided to the processor 108.

The image sensing section 106 senses a second portion of the laser, which is scattered on the wafer. The wafer surface inspecting apparatus in FIG. 3 may include more than one image sensing section 106. The image sensing section 106 converts a two-dimensional image into a digitalized image signaland the digitalized image signal is applied to the processor 108.

The processor 108 processes the digitalized image signal generated from the image sensing section 106, and the digitalized position signal generated from the position sensing section 104. That is, the processor 108 performs an image processing, and the processor 108 compares the digitalized position signal with reference position data to generate a position compensated value for adjusting the height of the wafer 100.

The position compensated value is generated by comparing position information of an inspection region of the wafer or position information of a next inspection region that is to be inspected with the reference position data corresponding to a previous spot. The position compensated value is provided to the system controller 112 via a bus line 114. The memory section 116 that stores the position compensated value may be connected to the bus line 114.

The system controller 112 controls the optical system 110 by an order of the processor 108. The system controller 112 also controls the wafer moving section 102, the position sensing section 104, and a clock generator (not shown) of the image sensing section 106.

The I/O controller 118 is also electrically connected to the bus line 114, and the I/O controller 118 controls an input section 120 and an output section 122.

FIGS. 4, 7 to 10 are a flow chart and schematic views showing a method of and apparatus for controlling a position before inspecting a wafer surface by two incident lights that are alternately irradiated in series according to a second embodiment of the present invention.

Figure 4:
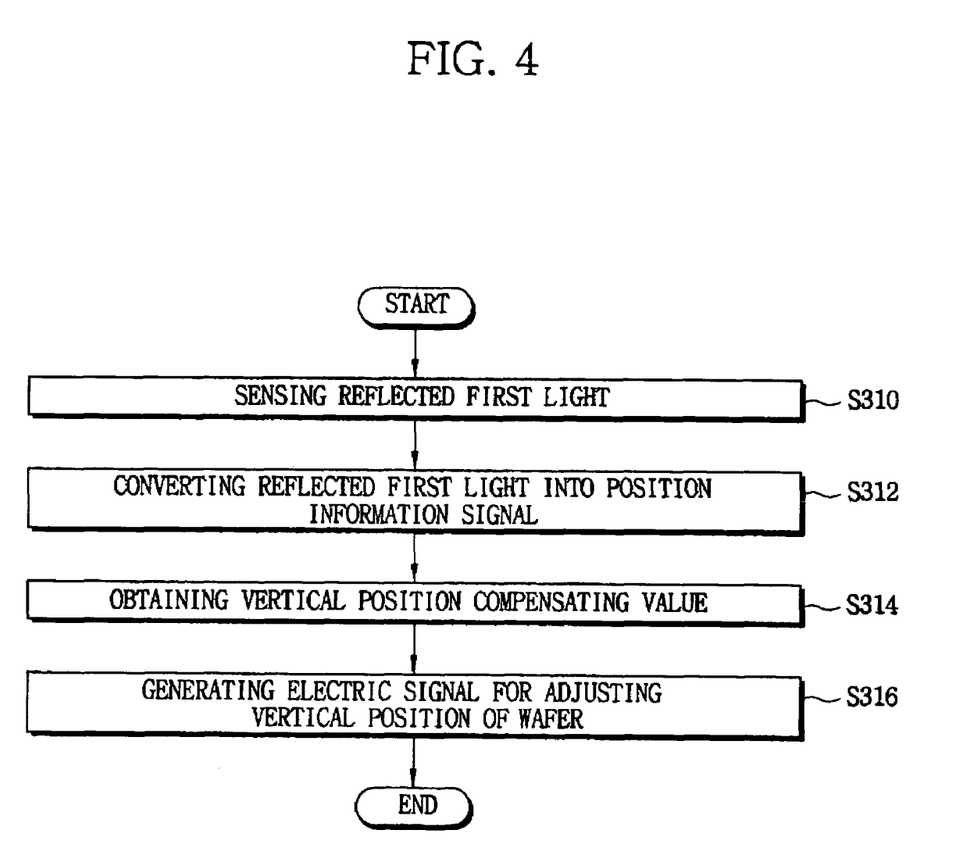
FIG. 4 is a flow chart showing a method of controlling a position before inspecting a wafer surface by using two incident lights that are alternately irradiated in series according to a second embodiment of the present invention.

FIG. 4 is a flow chart showing a method of controlling a position before inspecting a wafer surface by two incident lights that are alternately irradiated and arranged in series according to a second embodiment of the present invention.

Referring to FIG. 4, a first light for analyzing position of a wafer is reflected on an inspection region of a wafer. In step S310, the reflected first light is sensed, and in step S312, the reflected first light is converted into position information signal. In step S314, a vertical position compensating value of the wafer is obtained by a comparison of the position information signal and a reference value. Then in step S316, an electric signal for adjusting a vertical position of the wafer is generated from the vertical position compensating value, and the vertical position of the wafer is adjusted according to the electric signal.

Figure 7:
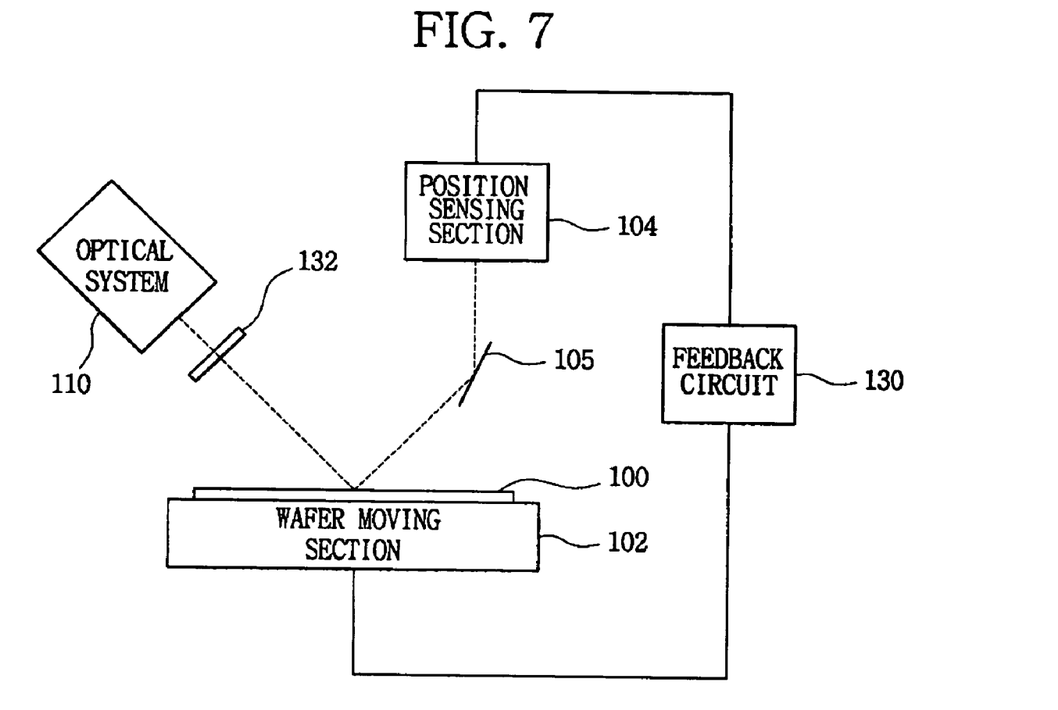
FIG. 7 is a schematic view showing an apparatus according to the second embodiment.
Figure 8:
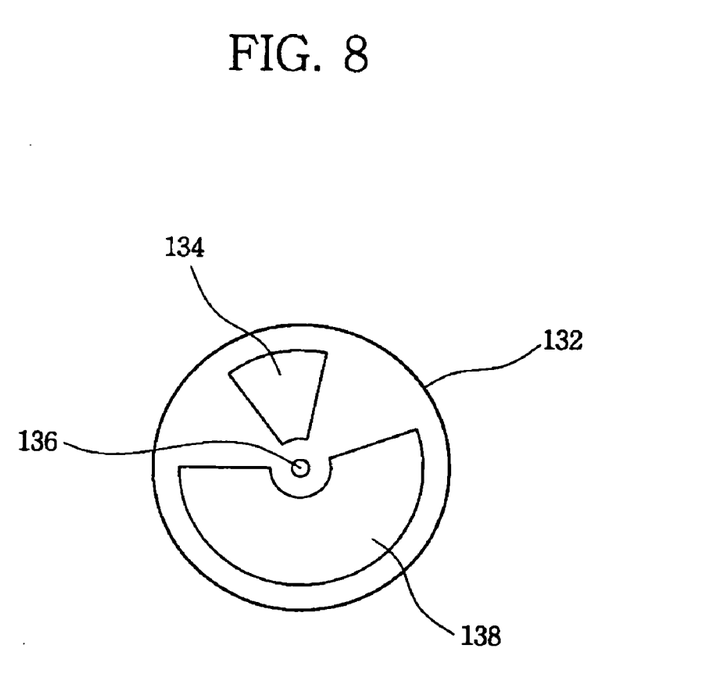
FIG. 8 is a plan view showing a chopper that divides an incident light into first and second rays arranged in series according to the second embodiment.

FIG. 7 is a schematic view showing an apparatus according to the second embodiment of the present invention, and FIG. 8 is a plan view showing a chopper that divides an incident light into first and second rays arranged in series according to the second embodiment.

Referring to FIG. 7, an optical system 110 irradiates an incident light that corresponds to a continuous wave having a specific period on an inspection region of a wafer 100, such that the incident light forms a specific angle with respect to the wafer 100. A chopper 132 divides the incident light into a first light for analyzing a position of wafer and a second light for inspecting the wafer surface. A reflected light that is reflected on the inspection region reaches the position sensing section 104 via a reflection mirror 105. Then, the position sensing section 104 generates a digitalized signal. The digitalized signal is provided to a feedback circuit 130, and a vertical position of the wafer is adjusted. The feedback circuit 130 includes a processor 108, a bus line 114, a memory section 116 and a system controller 112 (FIG. 3).

Referring to FIG. 8, the chopper 132 divides the incident light into the first light for analyzing a position of wafer and the second light for inspecting the wafer surface. The first light and the second light are arranged in series. The chopper 132 rotates with respect to a rotational axis 136 to have specific period. The chopper 132 has a circular plate shape having a first opening 134 for generating the first light, and a second opening 138 for generating the second light. The chopper 132 may include a plurality of first and second openings 134 and 138 in accordance with the period of the incident light and an angular velocity of the chopper 132.

Figure 9:
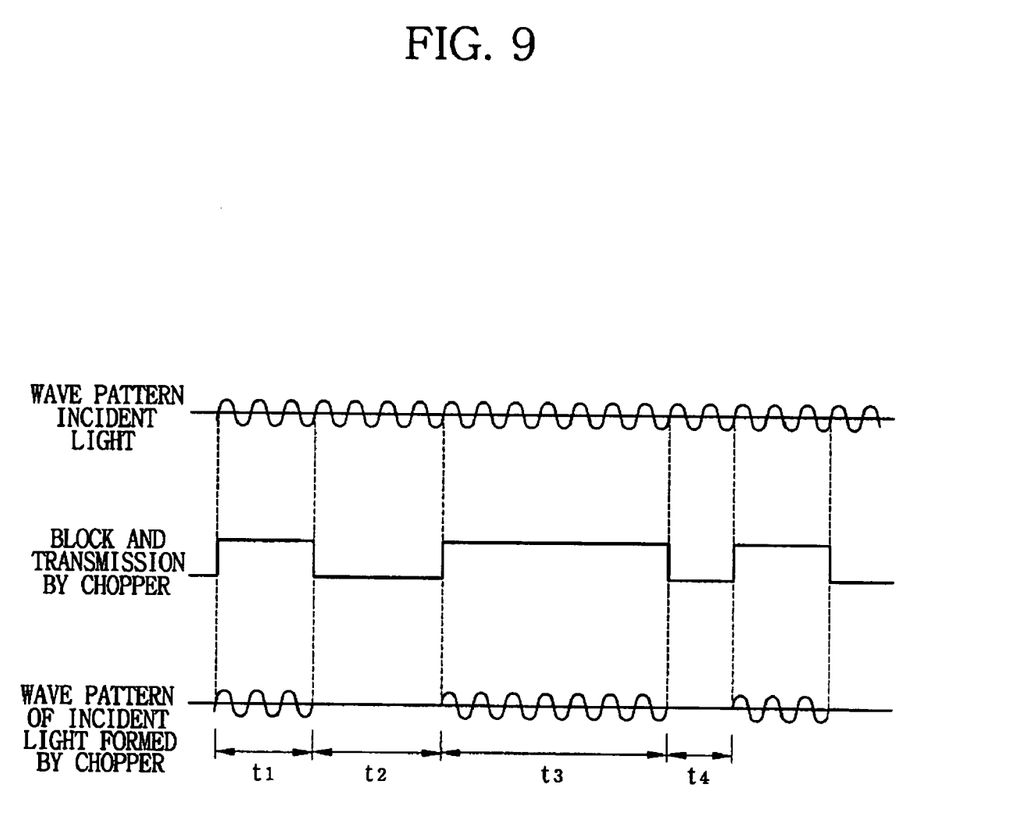
FIG. 9 is a timing diagram of the incident light formed in accordance with the second embodiment.

FIG. 9 is a timing diagram of the incident light formed in accordance with the second embodiment.

Referring to FIG. 9, the incident light corresponds to a continuous wave having a specific period. Preferably, a laser having wavelength in the range of about 360 nm to about 1 µm may be used as the incident light. The chopper 132 blocks the incident light or transmits the incident light. In detail, the incident light passes through the chopper during a first time $t_1$, the incident light is blocked during a second time $t_2$, the incident light passes through the chopper during a third time $t_3$, and the incident light is blocked during a fourth time $t_4$. The first time $t_1$ corresponds to the first opening 134, and the third time $t_3$ corresponds to the second opening 138 as shown in FIG. 8. The incident light of the first time $t_1$ corresponds to the first light for analyzing a wafer position, and the incident light of the third time $t_3$ corresponds to the second light for inspecting a wafer surface. Analyzing the wafer position and adjusting the vertical position of the wafer are performed during the second time $t_2$, and inspecting the wafer surface is performed during the third and fourth time $t_3$ and $t_4$. When the incident light having a specific spot is irradiated onto the inspection region of the wafer, the incident light of the first to fourth times $t_1$, $t_2$, $t_3$ and $t_4$ forms one frame.

Figure 10:
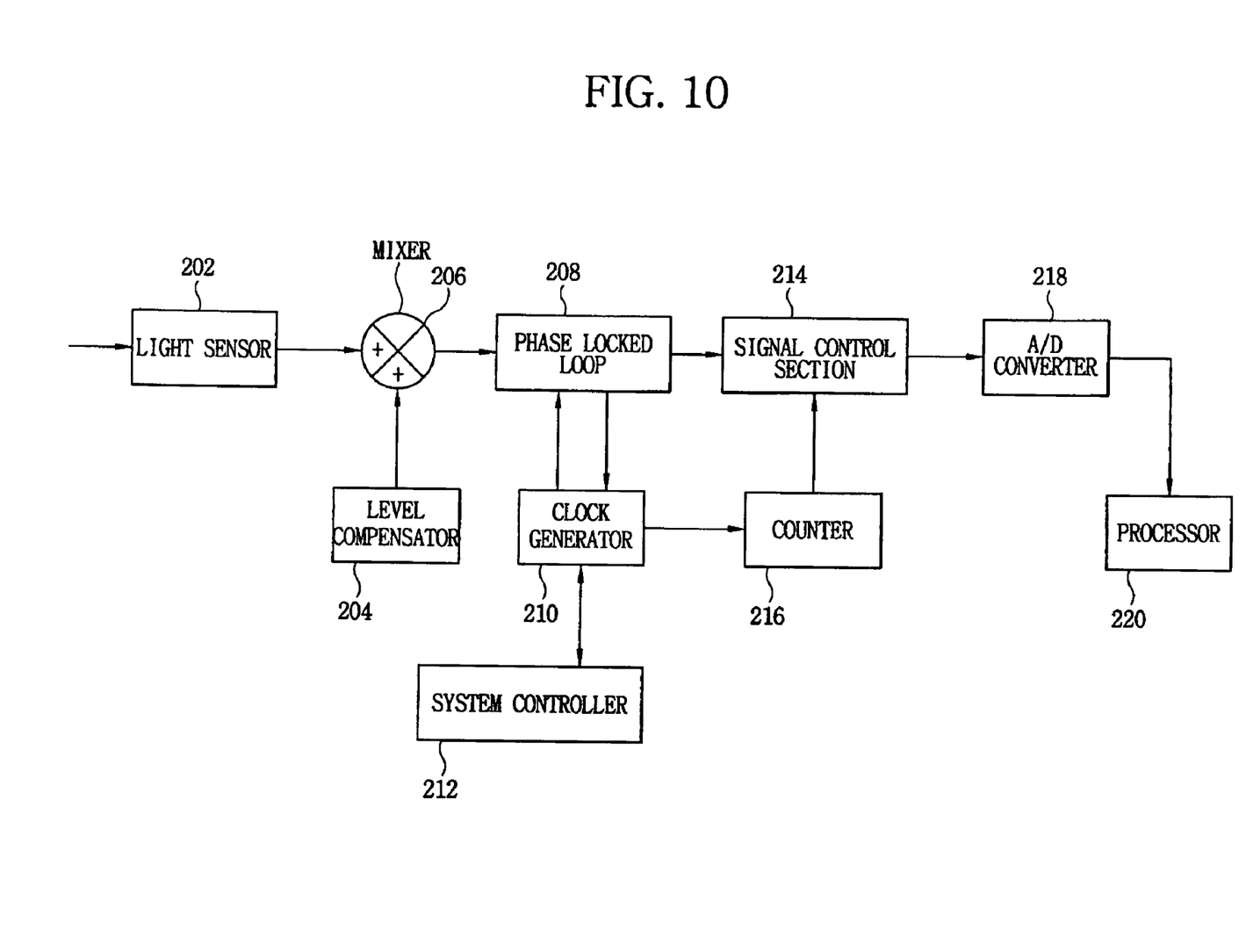
FIG. 10 is a block diagram showing an image sensing section in accordance with the second embodiment.

FIG. 10 is a block diagram showing an image sensing section in accordance with the second embodiment.

Referring to FIG. 10, a light sensor 202 senses a scattered light on the inspection region, which contains a two-dimensional image, and converts the scattered light into an electric signal corresponding to a first signal. A level compensator 204 compensates for a non-signal period caused by the second and fourth times $t_2$ and $t_4$.

A mixer 206 converts the outputs of the light sensor 202 and the level compensator 204 into a second signal that corresponds to a continuous signal. The second signal is provided to a phase locked loop 208. The clock generator 210 provides the phase locked loop 208 with a clock signal under a control of the system controller 212. The phase locked loop 208 generates a third signal having substantially the same phase as the second signal, and the phase locked loop 208 provides a signal control section 214 with the third signal. A clock signal that is adjusted to have substantially the same phase as the second signal is provided to a counter 216, so that the counter 216 generates a square wave for detecting an image signal from a reflected light. The square wave has a time interval corresponding to a signal caused by the second light in the third signal. The square wave is provided to the signal control section 214 to transmit the signal caused by the second light in the third signal. The signal caused by the second light is provided to an A/D converter 218. The A/D converter 218 generates a digital signal of one dimension, which corresponds to the second light. The digital signal is provided to a processor 220, and the processor 220 performs an image processing.

During the image processing, the digital signal is coded and compressed. Then, a high frequency region and noise are eliminated, and an image is formed. The image is die-to-die compared. That is, when inspecting the inspection region of the wafer is completed, the wafer is shifted in a horizontal direction, so that a next inspection region is inspected. Therefore, the inspection region of the wafer is checked.

Figure 5:
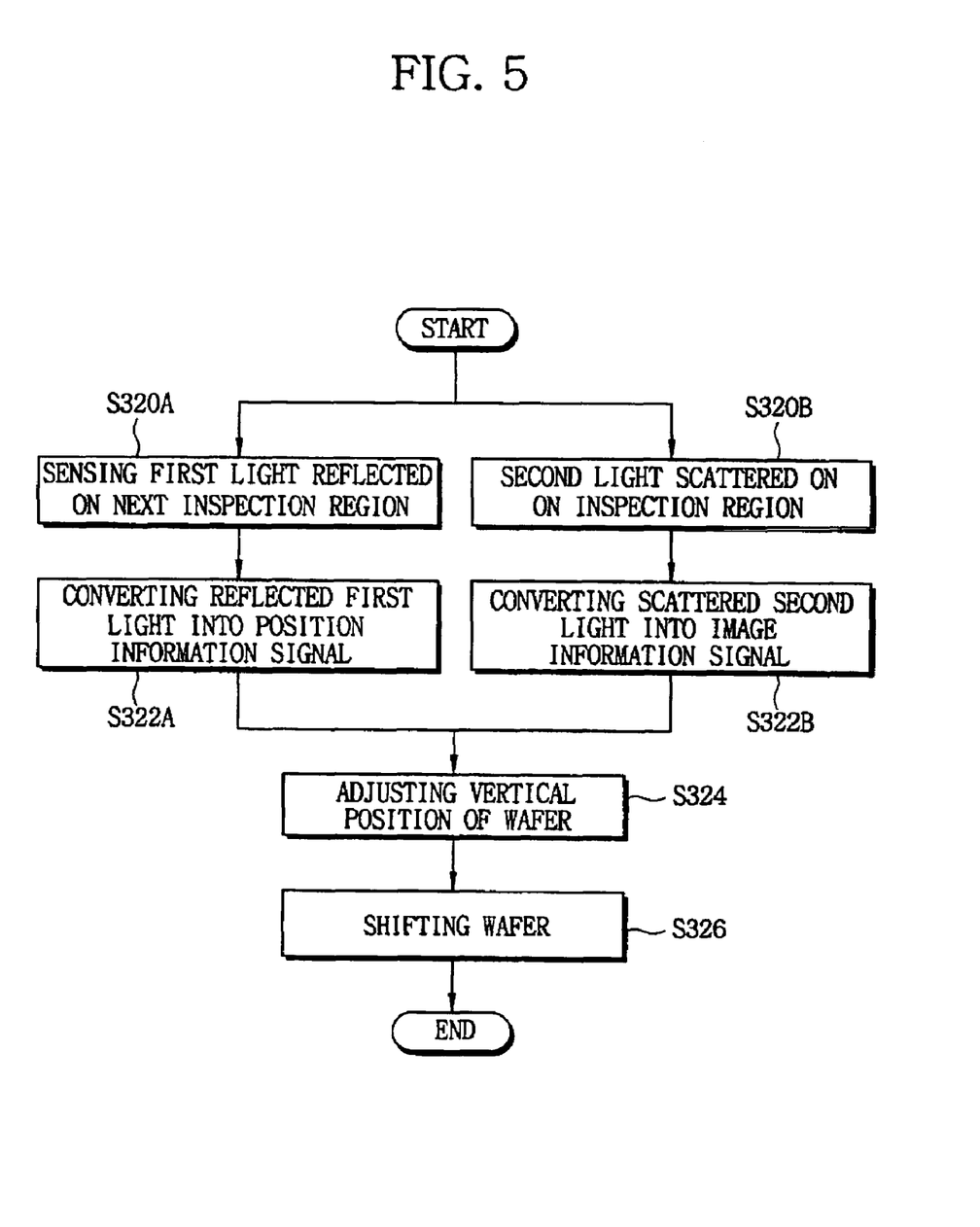
FIG. 5 is a flow chart showing a method of inspecting a wafer surface and simultaneously analyzing position of wafer by using two incident lights arranged in parallel according to a third embodiment of the present invention.
Figure 11:
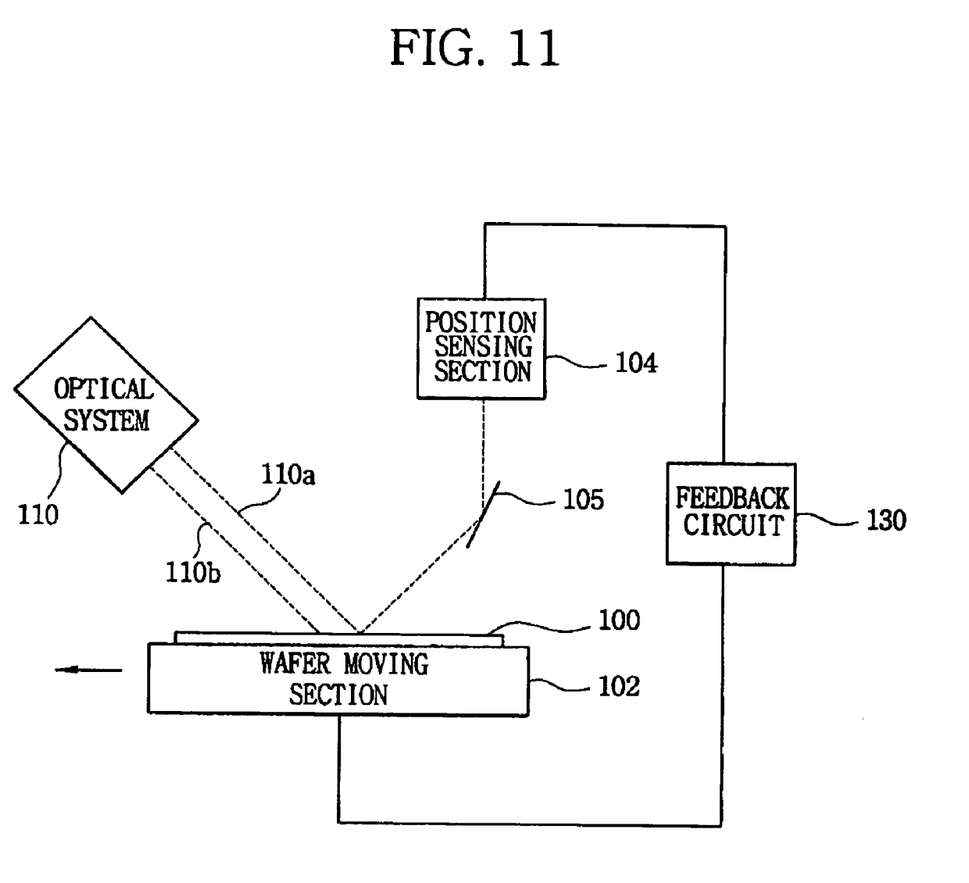
FIG. 11 is a schematic view showing an apparatus for simultaneous surface inspection and position analysis according to the third embodiment of the present invention.

FIGS. 5 and 11 are a flow chart and a schematic view showing a method and apparatus for simultaneously inspecting a wafer surface and analyzing the position of the wafer by using two incident lights arranged substantially parallel to each other according to a third embodiment of the present invention. In the present embodiment, inspection of a wafer surface is performed at an inspection region of a wafer, and analysis of a position of the wafer is performed at a next inspection region. Therefore, an optical system includes more than one laser. In detail, the optical system includes first and second lights. The first light is irradiated onto the next inspection region for reflection on the next inspection region to generate a position information signal, and the second light is irradiated onto the inspection region for scattering on the inspection region to generate an image information signal.

FIG. 5 is a flow chart showing a method of simultaneously inspecting a wafer surface and analyzing a position of the wafer by using two incident lights arranged substantially parallel to each other according to a third embodiment of the present invention.

Referring to FIG. 5, in step S320*a*, a first light that is reflected on a next inspection region is sensed, and in step S320*b*, a second light that is scattered on an inspection region is sensed. In step S322*a*, the reflected first light is converted into a position information signal, and in step S322*b*, and the scattered second light is converted into an image information signal. The image information signal may be generated simultaneously with the position information signal, or the image information signal may be generated after the position information signal.

Then, a vertical position of the wafer is adjusted in step S324 and the wafer is shifted, so that the next inspection region of the wafer is inspected through the same process. That is, the steps are repeated.

FIG. 11 is a schematic view showing an apparatus for simultaneous surface inspection and position analysis in accordance with the third embodiment.

Referring to FIG. 11, an optical system 110 irradiates at least two lights onto a wafer 100. A first light 110*a* is irradiated onto the wafer 100 in order to analyze a position of a next inspection region of the wafer 100, and a second light 110*b* is irradiated onto the wafer in order to inspect an inspection region of the wafer 100.

When the wafer 100 is shifted along an direction shown by the arrow in FIG. 11, the first light 110*a* is irradiated onto the next inspection region of the wafer 100, which is to be inspected when inspection of the inspection region is completed. Then, the first light 110*a* is reflected on the next inspection region. Further, the first light 110*a* reflected on the next inspection region is input to the position sensing section 104, so that the position sensing section 104 generates a position information signal. A reflection mirror 105 may reflect the first light 110*a* reflected on the next inspection region to guide the reflected first light 110*a* toward the position sensing section 104. The position information signal is provided to a feedback circuit 130 to control a wafer moving section 102. Therefore, a height of the wafer 100 is compensated for. The feedback circuit 130 includes a processor 108, a bus line 114, a memory section 116 and a system controller 112.

The second light 110*b* irradiated onto an inspection region of the wafer 100. The second light scattered at the inspection region of the wafer 100 is sensed by more than one image sensing section (not shown), and the image sensing section generates an image information signal.

A laser having a wavelength in the range from about 360 nm to about 1 μm may be used as the first and second lights 110*a* and 110*b*. Preferably, the first and second lights 110*a* and 110*b* may have different wavelengths from each other.

Figure 6:
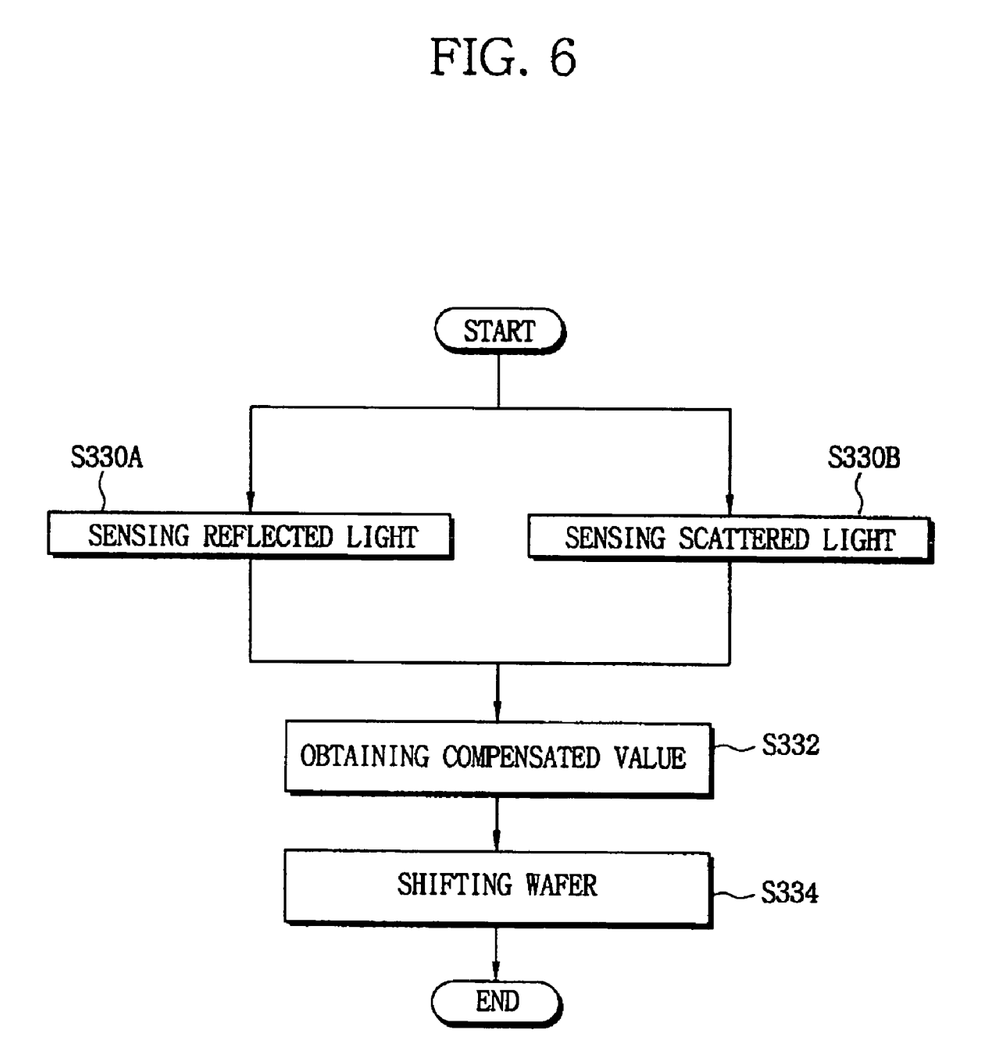
FIG. 6 is a flow chart showing a method of controlling a position of a wafer by anticipating a next inspection position via image processing of reflected light according to a fourth embodiment of the present invention.
Figure 12:
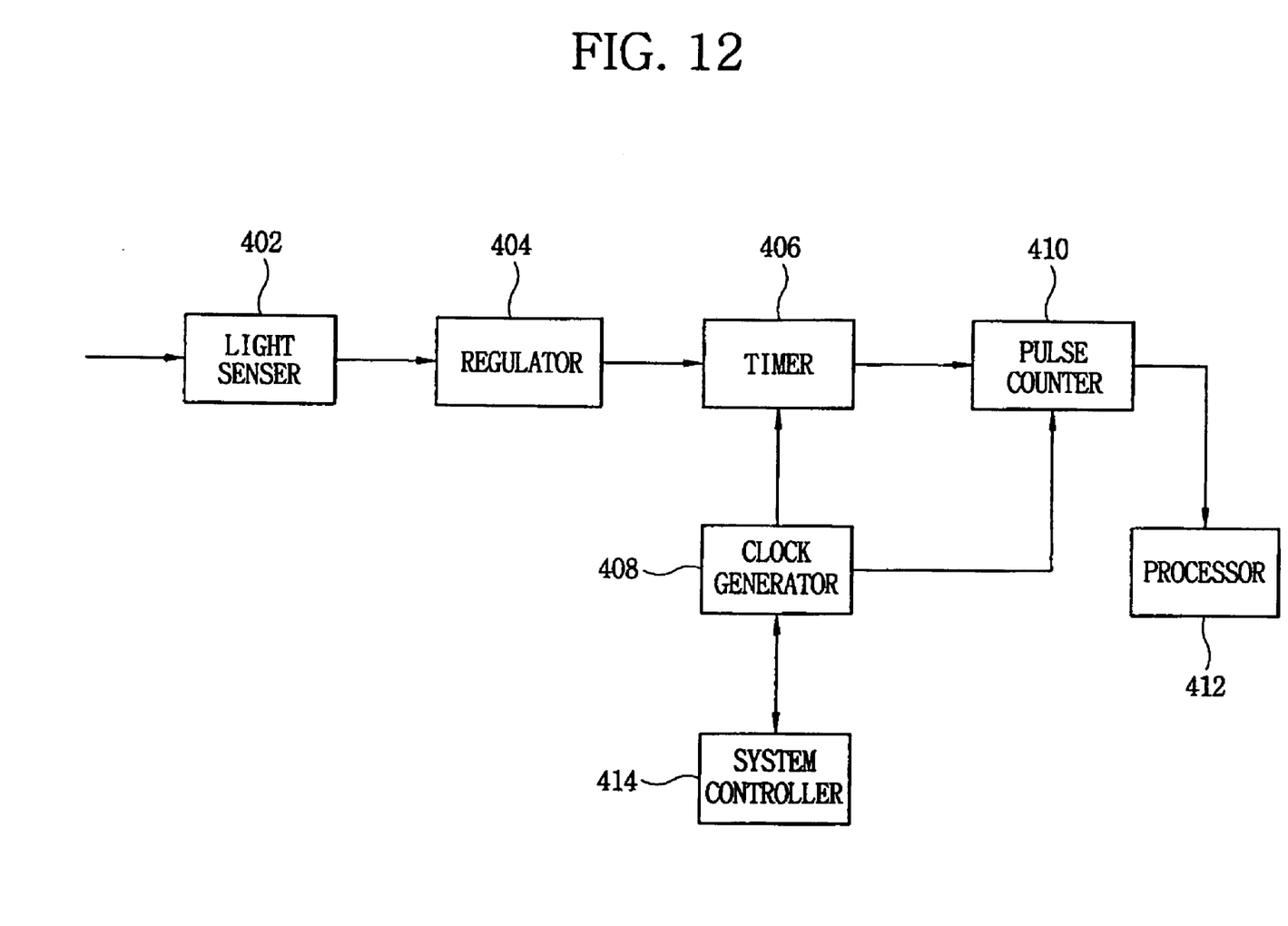
FIG. 12 is a block diagram showing a position sensing section that senses a reflected light reflected on an inspection region to convert the reflected light into a position information signal corresponding to the pulse series according to a fourth embodiment of the present invention.

FIGS. 6 and 12 are a flow chart and a block diagram showing a method and apparatus for controlling a position of a wafer by anticipating a next inspection position via image processing of reflected light that is reflected on a inspected position according to a fourth embodiment of the present invention.

According to the present embodiment, an incident light having a specific spot size is scattered and reflected on an inspection region. A first portion of the laser, which is scattered, is used for inspecting a wafer surface. A second portion of the laser, which is reflected, is used for analyzing a position of a next inspection position. The incident light may correspond to a laser having wavelength in the range from about 360 nm to about 1 μm.

FIG. 6 is a flow chart showing a method of controlling a position of a wafer by anticipating a next inspection position via image processing of reflected light that is reflected on a inspection position according to a fourth embodiment of the present invention.

Referring to FIG. 6, in step S330*a*, a reflected light is sensed at an inspection position, so that a vertical position of a wafer and an incline of a surface of the wafer are anticipated. Simultaneously in step S330*b*, a scattered light is sensed to generate an image information signal.

Furthermore, in step S332, a compensated value is obtained via the anticipated vertical position and the incline, and a vertical position and incline of the wafer are adjusted. Then, in step S334, the wafer is shifted, so that the next inspection position is inspected.

The position information signal is formed by image processing into a two-dimensional image having a circular shape with a specific area. When the incline of the wafer is different from a reference value, the area of the two-dimensional image is different from an area of a reference image. When a height of the wafer is different from a reference value, a center point of the two-dimensional image induces a deviation.

In order to perform the image processing, the processor requires pulse series or a digital value corresponding to the pulse series.

FIG. 12 is a block diagram showing a position sensing section that senses a reflected light reflected on an inspection region to convert the reflected light into a position information signal corresponding to the pulse series.

Referring to FIG. 12, an incident light having a specific cross-sectional area is reflected on an inspection region to reach at a light sensor 402 of a position sensing section, so that a first electric signal having vertical position information and incline information of a wafer is generated. The first electric signal is provided to a regulator 404. The regulator 404 converts the first electric signal into a square wave having a specific level. An interval generated during the square wave is substantially proportional to a spot size. The square wave is provided to a timer 406, so that the timer 406 outputs a pulse series having a specific period. A clock generator 408 provides the timer 406 with a clock signal under a control of the system controller 414. The pulse series is provided to a pulse counter 410, so that the pulse series is converted into a position information signal corresponding to a pulse count. The position information signal is then provided to a processor 412.

Then, vertical position and incline values of the wafer are anticipated via image processing of the position information signal, and the vertical position and the incline of the wafer are adjusted before inspecting a wafer surface.

According to embodiments of the present invention, position information of a wafer is examined and a position of the wafer is adjusted before inspecting a surface of inspection region of a wafer. Therefore, inspection of a wafer surface is accurately performed.

Although the illustrative embodiments have been described herein with reference to the accompanying drawings, it is to be understood that the present invention is not limited to those precise embodiments, and that various other changes and modifications may be affected therein by one of ordinary skill in the related art without departing from the scope or spirit of the invention. All such changes and modifications are intended to be included within the scope of the invention as defined by the appended claims.

What is claimed is:

1. A method for inspecting a wafer surface, comprising:
   loading a wafer into a chamber;
   irradiating light incident on the wafer including a first light for sensing a position of the wafer and a second light for inspecting a surface of the wafer;
   detecting the first light reflected on inspection region of the wafer to control the wafer position;
   detecting the second light scattered on the inspection region to inspect a surface of the inspection region of the wafer, wherein the first and second lights are alternately irradiated, the first light is irradiated before the second light, and control of the wafer position is performed prior to inspecting the surface of the inspection region;
   transforming the detected first light into a position information signal;
   obtaining a position compensating value by comparing the position information signal and a reference information signal;
   generating an electric signal for adjusting a position of the wafer on a basis of the position compensating value; and
   adjusting the position of the wafer by using the electric signal.

2. The method of claim 1, wherein the position is a vertical position.

3. The method of claim 1, further comprising:
   generating an image information signal from the scattered second light;
   checking defects of the surface of the inspection region based on the image information signal; and
   shifting the wafer in a predetermined direction to align the wafer for control of the position of the wafer.

4. The method of claim 3, wherein the predetermined direction is the horizontal direction.

5. The method of claim 3, wherein generating the image information signal comprises:
   transforming the scattered second light into a first signal containing information of the surface of the inspection region;
   generating a second signal by compensating for an interval caused by alternately irradiated incident light;
   compensating for a phase of the second signal with a clock;
   generating a third signal having a phase synchronized with a phase of the second signal;
   generating a square wave corresponding to a time interval of the second light included in the third signal;
   outputting a signal corresponding to the time interval of the second light by controlling the square wave; and
   digitalizing the signal corresponding to the time interval of the second light to output the image information signal.

6. A method for inspecting a wafer surface, comprising:
   loading a wafer into a chamber;
   irradiating light incident on the wafer including a first light for sensing a position of the wafer and a second light for inspecting a surface of the wafer; and
   detecting the first light reflected on a next inspection region of the wafer to control the wafer position while simultaneously detecting the second light scattered on an inspection region to inspect a surface of the inspection region of the wafer, wherein the first and second lights have different wavelengths from each other, and the first and second lights are simultaneously irradiated, wherein control of the wafer position and inspection of the surface of the inspection region are simultaneously performed, and the method further comprises:
   generating a position information signal in accordance with the first light reflected on the next inspection region and an image information signal in accordance with the second light scattered on the inspection region;
   adjusting a vertical position of the wafer; and
   shifting the wafer in a horizontal direction to align the wafer for further control of the wafer position.

7. A method for inspecting a wafer surface, comprising:
   loading a wafer into a chamber;
   irradiating light incident on the wafer including a first light for sensing a position of the wafer and a second light for inspecting a surface of the wafer;
   detecting the first light reflected on an inspection region of the wafer to control the wafer position;
   detecting the second light scattered on the inspecting region on to inspect a surface of the inspection region of the wafer;
   analyzing a vertical position and an incline of the wafer with the first, Light reflected on the inspection region for anticipating a vertical position and an incline of the next inspection region, wherein the first and second lights have the same frequency and a circular cross-sectional shape having a specific area;
   generating an image information signal from the second light scattered on the inspection region;
   shifting the wafer, whereby the next inspection region is moved to a position formerly occupied by the inspection region; and
   adjusting the vertical position and the incline of the wafer by the anticipated vertical position and incline.

8. The method of claim 7, wherein anticipating the vertical position and the incline of the next inspection region comprises:
   generating a first electric signal containing the vertical position and the incline of the wafer;
   converting the first electric signal into a square wave;
   generating a pulse series corresponding to a width of the square wave;
   counting the number of the pulse series to output a pulse number corresponding to a pulse disposed at a center of the square wave and to a width of the pulse;
   forming an image having a circular shape in accordance with the width and the center of the square wave; and
   comparing the image and a reference image to obtain compensation values for the next inspection region of the wafer.

9. An apparatus for inspecting a wafer surface, comprising:
   a wafer moving section for moving a wafer in the vertical direction and in the horizontal direction;
   an optical system for irradiating light incident on the wafer including a first light for sensing a vertical position of the wafer and a second light for inspecting the wafer surface;
   a position sensing section for sensing the first light reflected on the wafer to generate a position information signal;

an image sensing section for sensing the second light scattered on the wafer to generate an image information signal; and a feedback circuit for generating a value for adjusting the vertical position of the wafer, the feedback circuit providing the wafer moving section with the value for adjusting the vertical position of the wafer, wherein irradiation of the first and second lights is performed discontinuously, the first light is irradiated before the second light, and the wafer moving section is provided with the value for adjusting the vertical position of the wafer prior to inspecting the wafer surface.

10. The apparatus of claim 9, wherein the optical system comprises a chopper for generating the first and second lights, the chopper comprising:

a rotational axis;

a first opening for transmitting incident light, the incident light passing through the first opening for forming the first light; and a second opening for transmitting the incident light, the incident light passing through the second opening for forming the second light.

11. The apparatus of claim 9, wherein the image sensing section comprises:

a light sensor for sensing the second light scattered on the wafer to generate a first signal containing information about the wafer surface;

a level compensator for compensating a time interval caused by discontinuity of the light incident on the wafer to generate a compensated value;

a mixer for mixing the first signal generated from the light sensor and the compensated value generated from the level compensator to form a second signal that is continuous;

a clock generator for generating a clock signal;

a phase locked loop for receiving the second signal from the mixer and the clock signal from the clock generator, the phase locked loop synchronizing the clock signal with the second signal to generate a third signal;

a counter for receiving the clock signal synchronized with the second signal to generate a square wave;

a signal control section for receiving the third signal to generate a fourth signal corresponding to a time interval of the second light under a control of the square wave generated from the counter; and an analog-digital converter for digitalizing the fourth signal to output the image information signal.

12. The apparatus of claim 9, wherein the light incident on the wafer corresponds to a laser having a wavelength ranging from about 360 nm to 1 μm.

13. The apparatus of claim 9, further comprising a mirror for reflecting the first light reflected on the wafer toward the position sensing section.

14. The apparatus of claim 9, wherein the wafer moving section comprises:

a motor for roughly adjusting the wafer by the value for adjusting the vertical position of the wafer; and a piezoelectric device for precisely adjusting the wafer.

15. The apparatus of claim 9, wherein the feedback circuit comprises:

a processor for generating the value for adjusting the vertical position of the wafer and for checking for defects of an inspection region of the wafer by image processing;

a system controller for receiving the value for adjusting the vertical position of the wafer and for providing the wafer moving section with an analog signal; and a bus line for electrically connecting the processor and the system controller for transferring an electric signal between the processor and the system controller.

16. The apparatus of claim 15, further comprising a memory section for storing the value for adjusting the vertical position of the wafer, wherein the feedback circuit is electrically connected to the bus line.

17. The apparatus of claim 9, wherein the position information signal is digitalized.

18. An apparatus for inspecting a wafer surface, comprising:

a wafer moving section for moving a wafer in the vertical direction;

an optical system for irradiating light incident on the wafer including a first light for sensing a vertical position of the wafer and a second light for inspecting the wafer surface;

a position sensing section for sensing the first light reflected on the wafer to generate a position information signal;

an image sensing section for sensing the second light scattered on the wafer to generate an image information signal; and a feedback circuit for generating a value for adjusting the vertical position of the wafer, the feedback circuit providing the wafer moving section with the value for adjusting the vertical position of the wafer, wherein the first and second lights have different wavelengths from each other, and the first light is irradiated onto a next inspection region of the wafer while the second light is simultaneously irradiated onto an inspection region of the wafer.

19. An apparatus for inspecting a wafer surface, comprising:

a wafer moving section for moving a wafer in the vertical direction;

an optical system for irradiating light incident on the wafer including a first light for sensing a vertical position of the wafer and a second light for inspecting the wafer surface;

a position sensing section for sensing the first light reflected on the wafer to generate a position information signal;

an image sensing section for sensing the second light scattered on the wafer to generate an image information signal; and a feedback circuit for generating a value for adjusting the vertical position of the wafer, the feedback circuit providing the wafer moving section with the value for adjusting the vertical position of the wafer, wherein the light irradiated from the optical system has a specific cross-sectional area and the feedback circuit comprises an image processor for generating a compensated value of an incline of the wafer in accordance with a difference in area between an image of an inspection region and a reference image.

20. The apparatus of claim 19, wherein the position sensing section comprises:

a light sensor for sensing light for generating a first electric signal containing information including the vertical position and the incline of the wafer;

a regulator for receiving the first electric signal for generating a square wave;

a timer for outputting a pulse series corresponding to a width of the square wave;

a pulse counter for counting a number of the pulse series; and a clock generator for providing the timer and the pulse counter with a clock signal.

21. The apparatus of claim 19, wherein the image processor generates a compensated value of the vertical position of the wafer in accordance with a difference of a center point between the image of the inspection region and the reference image.

* * * * *